United States Patent [19]
Rotolo et al.

[11] Patent Number: 5,445,149
[45] Date of Patent: Aug. 29, 1995

[54] ELECTROCARDIOGRAPHY ELECTRODE POSITIONING DEVICE

[76] Inventors: Giuseppe Rotolo, Via Monte San Calogero 5; Gaspare A. Rotolo, Via dei Nebrodi, 61, both of Palermo, Italy, 90143

[21] Appl. No.: 64,274

[22] Filed: May 20, 1993

[30] Foreign Application Priority Data

May 22, 1992 [IT] Italy ................ MI92A1260

[51] Int. Cl.⁶ ................................. A61B 5/0408
[52] U.S. Cl. .......................... 128/644; 128/639
[58] Field of Search ............ 128/639, 644; 607/149

[56] References Cited
U.S. PATENT DOCUMENTS

| | | | |
|---|---|---|---|
| 3,534,727 | 10/1970 | Roman . | |
| 4,608,987 | 9/1986 | Mills | 128/639 |
| 5,054,496 | 10/1991 | Wen et al. | 128/639 X |
| 5,224,479 | 7/1993 | Sekine | 128/644 |

FOREIGN PATENT DOCUMENTS

| | | |
|---|---|---|
| 0396048 | 11/1990 | European Pat. Off. . |
| 2519856 | 7/1983 | France . |
| WO93/10706 | 6/1093 | WIPO . |

*Primary Examiner*—Lee S. Cohen
*Attorney, Agent, or Firm*—Jacobson, Price, Holman & Stern

[57] ABSTRACT

A sling or jacket (10) is to be worn on the bust and comprises internally a plurality of electrocardiographic recording electrodes (V1-V10) which, when wearing, are positioned in contact with predetermined bust areas. The sling (10) comprises a pectoral part (11) supporting a first series of electrodes of the plurality, an inguinal part (28) supporting a second series of electrodes of the plurality and a scapular part (36,37) supporting a third series of electrodes of the plurality and said parts being interconnected by straps for positioning and adjustment of the spacing.

30 Claims, 2 Drawing Sheets

ELECTROCARDIOGRAPHY ELECTRODE POSITIONING DEVICE

BACKGROUND OF THE INVENTION

In the art of electrocardiographic recordings one of the essential conditions for successful recording is the correct electrode positioning on the body and said positioning must therefore be made by a specially trained person.

But this can be a problem because, apart from the time required for this operation (the number of electrodes to be positioned can even by on the order of tens), trained personnel are not always available.

A typical example is the case of telemedicine, i.e. the reading of data to be sent, e.g. over the telephone line, to a special centre where the diagnosis is performed at a distance. This can be extremely useful for the control of patients with heart trouble with no need for them to go to the hospital or in case of localities without adequate medical facilities.

If in addition the patient is alone it is extremely difficult for him to position the electrodes, some in positions difficult to reach by oneself, even if he has been instructed beforehand about their correct positions.

The general purpose of the present invention is to obviate the above mentioned shortcomings by supplying an innovative device which would permit with simple movements correct and rapid positioning of all the electrodes necessary for an electrocardiographic recording.

SUMMARY OF THE INVENTION

In view of said purpose it has been sought to provide in accordance with the present invention a sling wearable on the bust and comprising internally a plurality of electrocardiographic recording electrodes positioned in contact with predetermined bust areas.

A sling provided in this manner can be further characterized in that it comprises a pectoral part supporting a first series of electrodes of the plurality, an inguinal part supporting a second series of electrodes of the plurality and a scapular part supporting a third series of electrodes of the plurality, said parts being interconnectable by straps for positioning and adjustment of the spacing.

To clarify the explanation of the innovative principles of the present invention and its advantages compared with the known art there is described below with the aid of the annexed drawings a possible embodiment by way of nonlimiting example applying said principles. In the drawings:

DETAILED DESCRIPTION OF THE DRAWINGS

Figure 1:
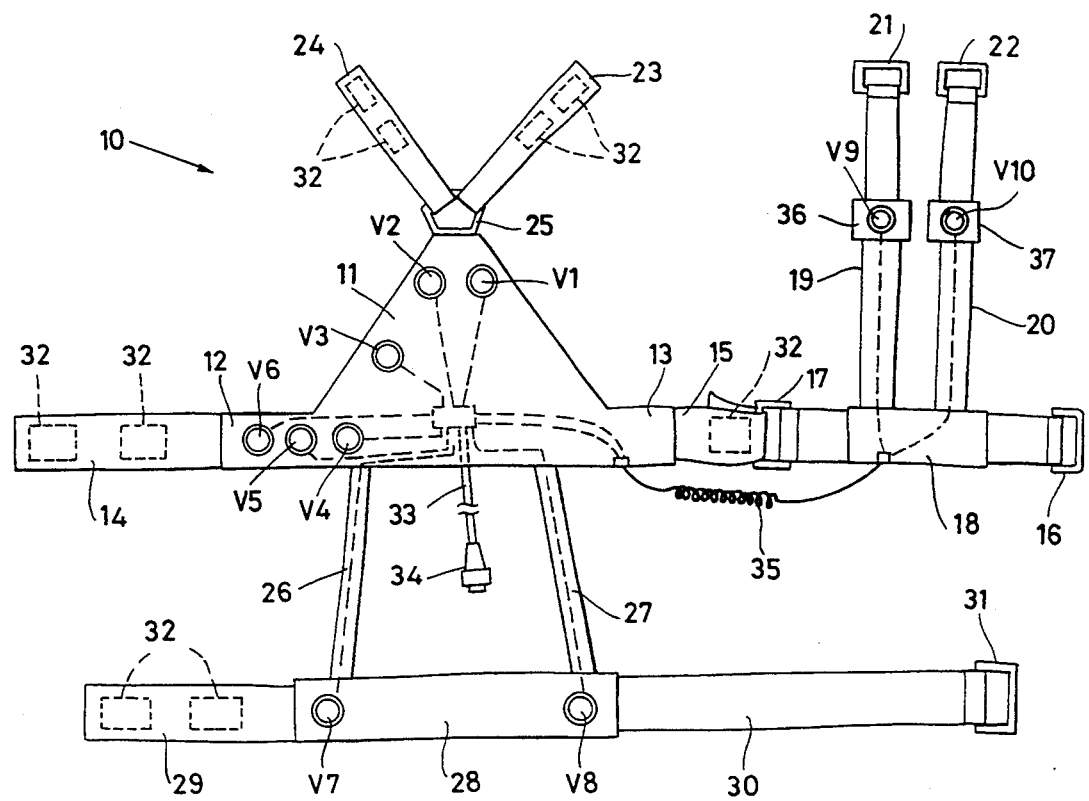
FIG. 1 shows an outstretched rear or internal view of a first embodiment of a positioning device in accordance with the present invention.

With reference to the Figures FIG. 1 shows, indicated as a whole by reference number 10, a positioning device in accordance with the present invention. Said device is made up of a sling to be worn on the bust and comprising a pectoral part 11, e.g. with substantially triangular shape at the base of which project in opposite directions tabs 12, 13 for connection to respective straps 14, 15 which engage (as shown for the right-hand part) in corresponding buckles 16, 17 supporting a rear element 18.

From the rear element 18 depart upward two rear straps 19, 20 terminating with buckles 21, 22 for engagement in corresponding front straps 23, 24 fixed to a front portion of the sling so as to provide two suspenders therefore.

For example, the front parts 23, 24 of the suspenders can be connected to the bib 11 by means of a ring 25 or the like.

From the bib 11 depart downward two other abdominal straps or bands 26, 27 for connecting with a transverse inguinal element 28 having a strap 29, 30 for fixing at the waist by means of a buckle 31.

Figure 2:
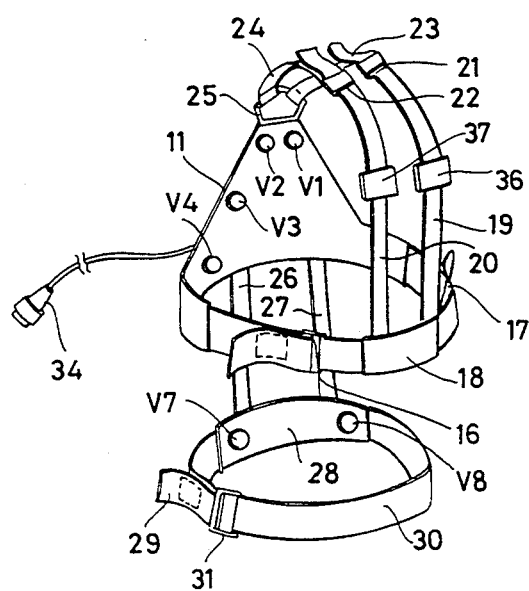
FIG. 2 shows a perspective view of the device of FIG. 1 once assembled.

The sling 10 can thus be shaped as shown schematically in FIG. 2 to be easily worn.

Although all the buckles can secure the corresponding straps by any known method, it has been found advantageous for rapidity of positioning to provide the straps with simple loops traversed by the straps which lead to the end of the selfadhesive strips 32 of the Velcro element type for folded back fixing as may be seen in FIG. 2. In this manner the strap ends folded toward the front sling part can be readily grasped and drawn even by the person wearing the sling with no need of help from others.

It is also advantageous that the straps be of elastic material so as to allow good sling adherence to the body.

As seen better in FIG. 2, on the pectoral part 11 is arranged a first series of electrodes made up for example from percordials V1–V6 arranged in accordance with international standards. On the inguinal part 28 is placed a second series of electrodes, e.g. consisting of two electrodes V7 and V8.

Finally, on the rear straps 19, 20 are placed scapular supporting parts 36, 37 for additional electrodes, e.g. one per suspender and indicated by reference numbers V9 and V10.

It is preferable that at least the pectoral part 11 and the inguinal 28 part be of flexible but not extensible material to allow said parts fitting to the human figure but without relative electrode position shifting thereon. Said material can be for example leather or nylon.

The series of electrodes shown are positioned on the sling in such a way that once worn and the straps tightened there will be the electrodes V1, V2 on the fourth intercostal space along the right and left parasternal line; the electrodes V4, V5, V6 level with the fifth intercostal space along the left hemiclavate, front axillary and media lines; the electrode V3 half way on the line between the electrodes V2, V4; the electrodes V7, V8 opposite the two iliac fossae; and the electrodes V9, V10 level with the scapulas.

All of the electrodes are connected with conductors optionally shielded and advantageously inside the sling to a multiconductor cable 33 also optionally shielded projecting from the sling and terminating with a connector 34 for connection to known electrocardiographic equipment. To allow adjustment of the buckles 17 the electrodes V9, V10 are connected to the cable 33 by means of a pair of spiralled cables 35 placed outside between the edge 13 and the rear element 18.

Figure 3:
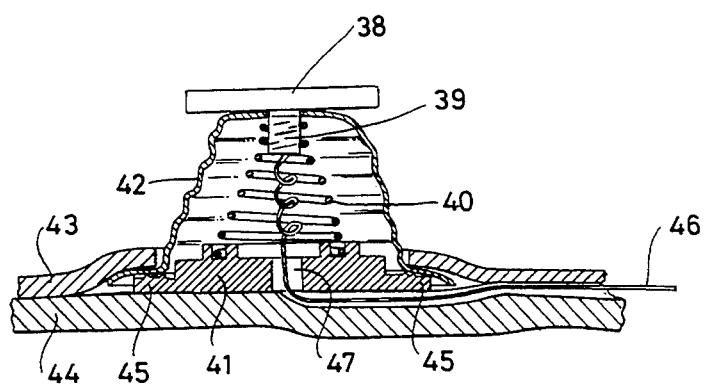
FIG. 3 shows a partially cross sectioned view of a detail of the device of FIG. 1.

FIG. 3 shows a possible embodiment of the electrodes. As may be seen in the figure the individual electrode is made up of a metal contact disc 38, e.g. of silver-plated brass, with a rear tang 39 on which is fixed the end of a thrust spring 40 with the other end received on a base 41 fixed on the corresponding sling part. To cover the spring and if necessary supply a certain lateral guide, between the disc 38 and the base 41 is placed a flexible sleeve 42 advantageously in bellows form provided for example of rubber, cloth or the like.

The sling part supporting the electrode can be provided in two superimposed layers 43, 44 receiving between them a peripheral edge 45 of the base 41 and the end of the bellows 42 so as to firmly block the electrode projecting from a hole in the layer 43. The insulated conductor 46 for electrode connection to the cable 33 passes between the layers 43, 44 and through a hole 47 in the base and is welded to the tang 39.

Thanks to the yielding assembly of the metal part of the electrode the necessary and stable electrical contact is assured between the metal surface and the skin of the person wearing the sling.

Figure 4:
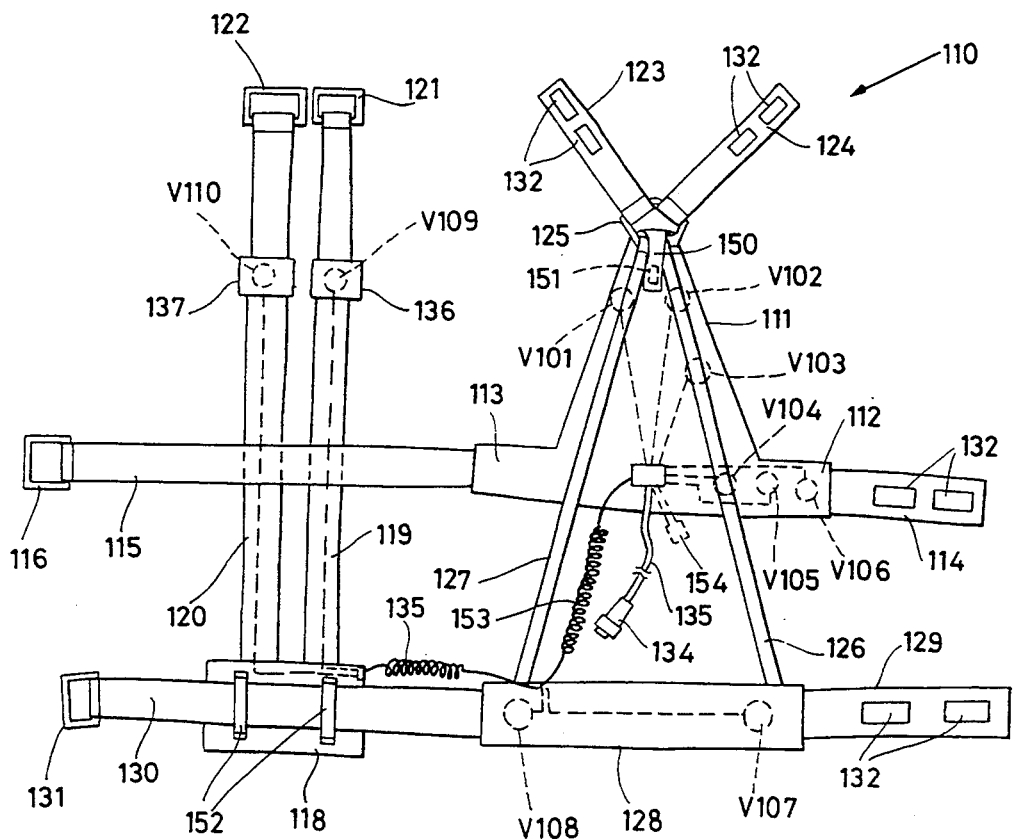
FIG. 4 shows a front view of a possible second embodiment of a device in accordance with the present invention.

FIG. 4 shows a second possible embodiment of a device or sling (indicated by reference number 110) in accordance with the present invention. For the sake of simplicity the various parts of the device 110 are indicated by the same reference numbers as the analogous parts of the device 10 with 100 added.

As may be seen in FIG. 4 the sling 110 shown from the outside comprises a transverse inguinal element 128 having a strap 129, 130 for fastening at the waist by means of a buckle 131.

On the strap 130 is placed by means of loops 152 a rear element 118 sliding to allow centring on the back and from which depart upward two rear straps 119, 120 terminating with buckles 121, 122 for engagement in corresponding front straps 123, 124 so as to provide two suspenders.

The front ends of the suspenders are connected to a ring 125 which is in turn connected through two more straps or abdominal bands 126, 127 to the inguinal strip 128. This provides a first sling part which can be worn alone to position the electrodes V107, V108 supported by the strip 128 opposite the iliac fossae and scapular electrodes V109, V110 supported by elements 136, 137 on the suspenders 119, 120 opposite the scapula.

The sling 110 comprises a second or pectoral part 111 at the base of which project in opposite directions tabs 112, 113 for connection to respective straps 114, 115 which engage together by means of a buckle 116 and adhesive strips 132 of the Velcro type.

The pectoral part 111 has at the top a ribbon 150 with Velcro or other blocking means, e.g. a snap, to secure in a removable manner the upper end of the pectoral part to the ring 125. Advantageously the pectoral part 111 passes between the patient's chest and the straps 126, 127 so that the latter press it effectively against the chest.

The pectoral part 110 supports a plurality of electrodes V101-V106 arranged substantially like the electrodes V1-V6 of the pectoral part 10. Said electrodes are connected by conductors optionally shielded and advantageously inside the sling to a multiconductor cable 133 also optionally shielded projecting from the sling and terminating with a connector 134 for connection to known electrocardiographic equipment.

The electrodes V109, V110 are connected to the cable 133 through an outside cable segment 135 and, together with the electrodes V107, V108 through an outer cable segment 153. Advantageously the cables 135 and 153 are the spiralled stretching type. Naturally all the electrodes can be of the type shown in FIG. 3.

The complete device of FIG. 4 can be worn in the same manner as shown in FIG. 1. In addition the sling 110 allows uncovering of the patient's chest so as to allow for example external heart massage or the application of defibrillation plates. To achieve this it is sufficient to release the ribbon 150 from the ring and open the strap 114, 115 to completely draw out the part 111. Even when the pectoral part 111 is in nonoperating position or removed the remaining electrodes in contact with the patient's body allow electrocardiogram recording which, although partial, nevertheless allows observation of the patient's heart condition.

To extend the functions of the positioning device in the case for example of hospital use there can also be provided another connector 154 with terminals connected in parallel to electrodes of the pectoral part 111 or they can even lead separately to the connector 134. If necessary, to said additional connector 154 there can be connected known individual electrodes arranged at different points on the body as compared with the plurality of electrodes supported by the sling. For example this could be useful if it is necessary to remove the bib 111 while it is necessary to perform recordings in the pectoral area.

At this point it is clear that the pre-set purposes have been achieved by providing a device allowing easy and quick positioning of electrodes for Electrocardiography. Indeed, it is sufficient to put on the sling to achieve automatic positioning of the electrodes in the correct positions.

Thanks to the adjustability of the straps forming the sling it is possible to fit it to a reasonable range of body types. Optionally there can be provided a limited number of models of different dimensions, e.g. for babies, children and adults, so as to always assure correct positioning of the electrodes even for greater variations of body type. Optionally, with a system similar to that shown, even the abdominal straps 26, 27 can be provided adjustable to fit the sling in case of large variations in the height of the bust.

It is clear how it is easy for anyone, even without special training, to wear of cause to wear the sling and, connected to a measuring apparatus, perform an electrocardiogram.

The excellent adherence of the electrodes to the skin which is assured by the yielding support thereof and the form of the sling allows dispensing with the usual skin preparation procedures such as depilation, grease removal, etc Moreover it is not necessary to use the known conductive pastes, further simplifying application of the electrodes as compared with the known art.

Due to the excellent adherence and firm electrode positioning it is possible to perform electrocardiograms even on seated or standing persons, in contrast with the known techniques with individual electrodes which make necessary reading only on prone persons.

Naturally the above description of an embodiment applying the innovative principles of the present invention is given merely by way of example and therefore is not to be taken as a limitation of the patent right claimed here.

For example, the exact configuration of the supports, straps and buckles can change depending on the specific construction and application requirements and the electrical connection between the electrodes and the electrocardiographic machine can vary in the same manner.

Although the sling described is made up of a plurality of straps connecting otherwise separate elements, it is clear that it would also be possible to conceive of a device in the form of a corset more or less closed with extensible connecting parts for the electrode supports. For example, the corset can be provided optionally in the form of a complete jacket or "vest" made for example of elasticised material for fitting to the body type of the person and the adjusting straps can also be eliminated.

As will be clear to those skilled in the art it is also conceivable to place on each strap two kinds of buckles, a first buckle for fitting to the body type and a second buckle for easy sling opening and closing for putting it on with ease. This is particularly useful in case of patients who must perform the electrocardiogram periodically and alone. Indeed, once the sling is adjusted with the first kind of buckle for his own body type, to wear it is sufficient to open and close with quick movements the second kind of buckle.

In addition, the chest strap 14, 15 can also comprise a single adjusting buckle and the rear element 18 can be sliding thereon by means of loops so it can be centred on the back as the chest circumference of the user changes.

Finally, to supply perfect adherence of the sling to the bust it is not necessary that the entire length of the straps and suspenders be of elastic material but only a section thereof.

We claim:

1. Device to be worn on a bust for positioning a plurality of electrocardiographic recording electrodes in contact with predetermined areas of the bust, said device comprising:
   a plurality of electrocardiographic recording electrodes,
   holding means for holding said electrocardiographic recording electrodes against a predetermined area of the bust
   each of said plurality of electrocardiographic recording electrodes includes a contact plate biased by a spring toward an interior of the device and a supporting plate on which said spring reacts for thrust of the contact plate, the supporting plate being peripherally received between superimposed layers of the holding means and between the contact plate and the supporting plate extends a protective bellows element receiving said spring.

2. Device in accordance with claim 1, wherein all of said plurality of electrocardiographic recording electrodes are connected to a multiconductor cable adapted to be connected to an electrocardiographic apparatus.

3. Device in accordance with claim 2, further comprising a connector electrically connected to said multiconductor cable.

4. Device to be worn on a bust for positioning a plurality of electrocardiographic recording electrodes in contact with predetermined areas of the bust, said device comprising:
   a pectoral part supporting a first series of electrocardiographic recording electrodes,
   an inguinal part supporting a second series of electrocardiographic recording electrodes, and
   a scapular part supporting a third series of electrocardiographic recording electrodes,
   said pectoral part extending laterally in a strap for fastening around a chest, and
   a rear element supported by said strap supporting said scapular part between said rear element and said pectoral part,
   said pectoral part, said inguinal part and said scapular part being connected to effect positioning at their respective labelled body locations.

5. Device in accordance with claim 4, wherein said pectoral part, said inguinal part, and said scapular part are interconnected by extensible connection parts to allow their adherence to the bust.

6. Device in accordance with claim 5, wherein said connection parts comprise straps for positioning and adjustment of spacing between the interconnected pectoral, inguinal, and scapular parts.

7. Device in accordance with claim 6, wherein at least one section of at least one connection strap is made of elastic material.

8. Device in accordance with claim 6, wherein at least one of the positioning and adjustment straps comprises buckles for adjustment of its length.

9. Device in accordance with claim 8, wherein said buckles comprise means of engagement made up of strips of hook and loop fabric.

10. Device in accordance with claim 6, wherein said straps comprise a pair of suspenders for passage over the shoulders.

11. Device in accordance with claim 10, wherein said third series of electrodes are each supported by one of said suspenders.

12. Device in accordance with claim 10, wherein said suspenders extend between said rear element and a front portion of the device.

13. Device in accordance with claim 12, wherein said front portion is connected in a position above said pectoral part.

14. Device in accordance with claim 13, wherein said pectoral part and said front portion are connected by a releasable connector.

15. Device in accordance with claim 14, wherein said releasable means comprises an opening ribbon fastened to said pectoral part passing through a ring supported on said front portion.

16. Device in accordance with claim 4, wherein said pectoral part is of nonextensible material to hold a spacing of the electrocardiographic recording electrodes thereon fixed.

17. Device in accordance with claim 4, wherein said first series of electrocardiographic recording electrodes comprises two electrodes located spaced for positioning near the fourth intercostal space along the right and left parasternal line respectively; three electrocardiographic recording electrodes spaced for positioning substantially level with the fifth intercostal space along the left hemiclavate, front axillary and media lines respectively; and an electrocardiographic recording electrode placed for positioning substantially halfway on the conjunction line of the electrode placed along the left parasternal line with the electrode placed along the left hemiclavate line when said pectoral part is positioned on a body.

18. Device in accordance with claim 4, wherein said inguinal part is of nonextensible material to hold a spacing of the electorcardiographic recording electrodes thereon fixed.

19. Device in accordance with claim 4, wherein said second series of electrocardiographic recording electrodes comprises two electrodes placed for positioning substantially opposite the two iliac fossae when said inguinal part is positioned on a body.

20. Device in accordance with claim 4, wherein said third series of electrocardiographic recording electrodes comprises two electrodes each placed for positioning substantially opposite a scapula when said inguinal part is positioned on a body.

21. Device in accordance with claim 4, wherein said inguinal part extends laterally in a strap for fastening around a waist.

22. Device in accordance with claim 2, wherein said strap for chest fastening comprises two adjusting buckles placed at opposite sides of said rear element.

23. Device in accordance with claim 2, wherein said rear element is supported on said strap or in a sliding manner thereon.

24. Device in accordance with claim 23, wherein said pectoral part is connected to said inguinal part through front abdominal straps.

25. Device in accordance with claim 4, wherein said pectoral part is connected to said inguinal part through front abdominal straps.

26. Device in accordance with claim 4, wherein said pectoral part is at least partially removable to be movable to a nonoperating position uncovering a pectoral area of the bust.

27. A device to be worn on a bust for positioning a plurality of electrocardiographic recording electrodes in predetermined areas of the bust, said device comprising:
   a pectoral part supporting a first series of electrocardiographic recording electrodes,
   an inguinal part supporting a second series of electrocardiographic recording electrodes, and
   a scapular part supporting a third series of electrocardiographic recording electrodes,
   said pectoral part having a triangular shape with a lower base extending laterally in a strap for fastening around a chest, and an upper vertex connected to a pair of suspenders for passage over the shoulders, said suspenders supporting at a back said scapular part,
   said inguinal part extending laterally in a strap for fastening around the waist and connected to said pectoral part through front abdominal straps.

28. A device to be worn on a bust for positioning a plurality of electrocardiographic recording electrodes in contact with predetermined areas of the bust, said device comprising:
   a pectoral part supporting a first series of electrocardiographic recording electrodes,
   an inguinal part supporting a second series of electrocardiographic recording electrodes,
   a scapular part supporting a third series of electrocardiographic recording electrodes, and
   a rear element supported by a strap for fastening around a chest, said strap including two adjusting buckles placed on opposite sides of said rear element.
   said pectoral part, said inguinal part and said scapular part being connected to effect positioning at their respective labelled body locations.

29. A device to be worn on a bust for positioning a plurality of electrocardiographic recording electrodes in contact with predetermined areas of the bust, said device comprising:
   a pectoral part supporting a first series of electrocardiographic recording electrodes,
   an inguinal part supporting a second series of electrocardiographic recording electrodes,
   a scapular part supporting a third series of electrocardiographic recording electrodes,
   said inguinal part having a laterally extending strap for fastening around a waist, and
   suspenders extending between a rear element and said pectoral part, said rear element being supported on said strap for waist fastening,
   said pectoral part, said inguinal part and said scapular part being connected to effect positioning at their respective labelled body locations.

30. A device to be worn on a bust for positioning a plurality of electrocardiographic recording electrodes in contact with predetermined areas of the bust, said device comprising:
   a pectoral part supporting a first series of electrocardiographic recording electrodes,
   an inguinal part supporting a second series of electrocardiographic recording electrodes, and
   a scapular part supporting a third series of electrocardiographic recording electrodes,
   said pectoral part including support means extending laterally for fastening said pectoral part on a chest,
   said inguinal part including support strap means extending laterally for fastening said inguinal part on a waist,
   means for supporting said scapular part on the back and for connecting said pectoral part with at least one of said support means of said pectoral part and said support means of said inguinal part.

* * * * *